United States Patent [19]

den Hartog et al.

[11] Patent Number: 4,985,423
[45] Date of Patent: Jan. 15, 1991

[54] NEW 1,4-DIAZEPINE DERIVATIVES HAVING ANIT-ULCER ACTIVITY

[75] Inventors: Jacobus A. J. den Hartog; Herman H. van Stuivenberg; Ineke van Wijngaarden, all of Weesp, Netherlands

[73] Assignee: Duphar International Research B.V., Weesp, Netherlands

[21] Appl. No.: 374,775

[22] Filed: Jul. 3, 1989

[30] Foreign Application Priority Data

Jul. 7, 1988 [NL] Netherlands ................ 8801716

[51] Int. Cl.$^5$ ................ C07D 471/04; C07D 495/04; C07D 495/14; C07D 493/04
[52] U.S. Cl. ................ 514/219; 514/220; 514/926; 514/927; 540/555; 540/557; 540/568
[58] Field of Search ................ 514/220, 219; 540/557, 540/555

[56] References Cited

U.S. PATENT DOCUMENTS 4,486,591 12/1984 Chakrabarti ................ 540/557
4,820,690 4/1989 Gregory ................ 514/926

OTHER PUBLICATIONS

Ried, Chem., Ber III, 1521-26 (1978).
Gatta et al., J. Het. Chem. 20, 1251 (1983).

*Primary Examiner*—Mark L. Berch
*Attorney, Agent, or Firm*—Stevens, Davis, Miller & Mosher

[57] ABSTRACT

The invention relates to a group of new 1,4-diazepine derivatives of the formula

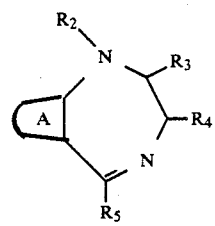

wherein A represents a group of the formulae 2-10

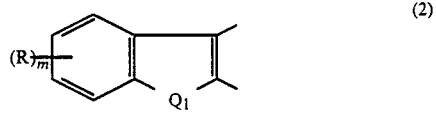

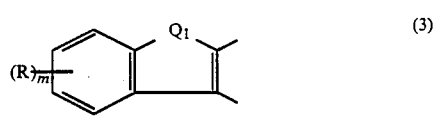

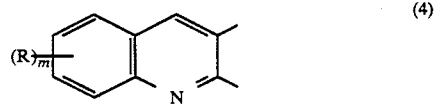

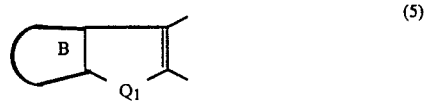

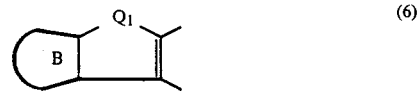

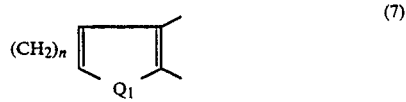

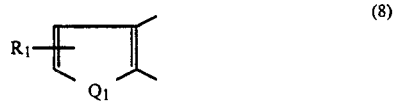

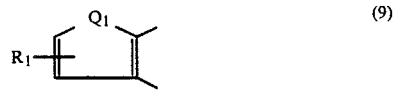

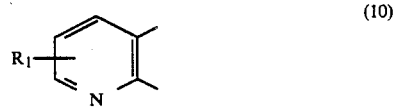

These compounds have a strong anti-ulcer activity after oral administration.

4 Claims, No Drawings

NEW 1,4-DIAZEPINE DERIVATIVES HAVING ANIT-ULCER ACTIVITY

The invention relates to a group of new 1,4-diazepine derivatives and salts and prodrugs thereof having favourable properties on ulcers in the gastrointestinal tract, to compositions which comprise these compounds as an active substance, and to the preparation of the said compounds.

Ulcerations of the stomach and the duodenum are a frequently occurring syndrome in human beings. The objects of pharmaco-therapeutic treatment of these disorders are: relieving pain, curing the ulcer, and preventing recurrence of the symptoms.

Present-day pharmaco-therapy is mainly directed to inhibiting the secretion of one of the aggressive factors in stomach and duodenum, namely the gastric acid. The histamine $H_2$-antagonists like cimetidine and ranitidine are the best known examples hereof. Besides, a few pharmaco-therapeutic substances are known which have so-called mucosa-protective properties. This means that the said substances, in oral dosages which do not inhibit gastric acid secretion, favourably influence one or more of the factors which contribute to a correct balance between aggressive effects (for example, gastric acid, pepsin, bile acids) and defensive effects (for example, mucus secretion, bicarbonate secretion, blood circulation) on the mucosa of stomach and duodenum. The best known examples hereof are sucralphate and bismuth subcitrate.

It is the object of the present invention to provide compounds which have a combination of the above-described properties i.e.

cause inhibition of gastric acid secretion, for example by a reversible inhibition of the $(H^+ + K^+)$-ATPase system in the stomach.

have a so-called mucosa-protective effect.

Both effects should occur after oral administration and should continue for a sufficiently long period of time.

On the basis of their properties such compounds could also be used for one or more of the following disorders: gastritis, duodenitis, reflux oesophagitis, non-ulcer dyspepsia and the Zollinger-Ellison syndrome.

It has now been found surprisingly that the compounds of formula 1 hereinafter and their acid addition salts satisfy the objects mentioned hereinbefore.

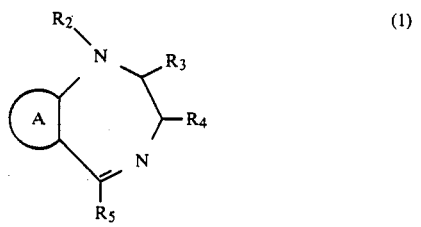

(1)

In formula 1 the symbols used have the following meanings:

A together with the two carbon atoms of the seven membered ring, forms a group of the formulae 2-10

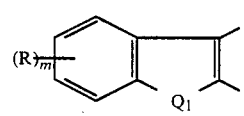
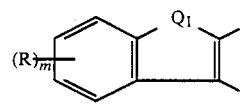
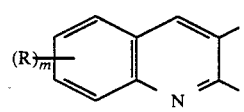
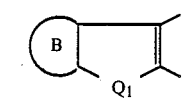
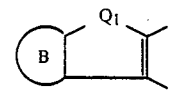
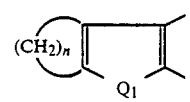
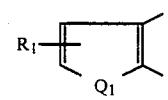
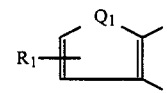
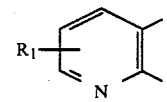

wherein

R is halogen, alkyl, alkoxy, alkylthio, amino, mono- or dialkylamino, hydroxyalkyl. alkylcarbonyl, aminocarbonyl, mono, or dialkylamino carbonyl, alkoxycarbonyl, nitro, cyano, trifluoromethyl, trifluoromethoxy, alkylsulphonyl, aminosulphonyl, hydroxy, alkylene dioxy, phenyl or benzoyl, and m has the value 0–4, $Q_1$ is oxygen or sulphur, B together with the two carbon atoms of the five membered ring, is thienyl or pyridyl, which groups may be substituted with a group $(R)_m$, $R_1$ is a phenyl group optionally substituted with group $(R)_m$, n has the value 3 or 4;

$R_2$ is hydrogen, alkyl, phenylalkyl, alkylcarbonyl, aminocarbonyl, mono- or dialkylaminocarbonyl, alkoxycarbonyl or alkoxycarbonylalkyl;

$R_3$ and $R_4$ independently of each other are hydrogen, alkyl or hydroxy; and $R_5$ is phenyl, thienyl, cyclopentyl, cyclohexyl, n-pentyl, n-hexyl, benzyl, phenethyl, phenylethenyl, phenylamino, or benzylamino, which groups may be substituted with a group $(R)_m$.

When in the above formula (1) $R_2$ is hydrogen, tautomerism may occur in the diazepine ring. As a result of the occurrence of the said tautomerism, an optional group $R_2$ having a meaning different from hydrogen, may be bonded to the other nitrogen atom of the diazepine ring. In so far as tautomerism is concerned, the invention relates to compounds substituted with a group $R_2$ which is present either at the nitrogen atom in position 1 or at the nitrogen atom in position 4.

When groups $R_3$ and/or $R_4$ in the above formula (1) have a meaning different from hydrogen, the carbon atoms to which $R_3$ and/or $R_4$ are bonded are chiral centres. In so far as chiral centres are concerned, the invention relates to the various enantiomers of the compound of formula 1 and to racemic mixtures of the said compounds.

On the basis of their properties the invention preferably relates to compounds of formula 1, wherein R, $Q_1$, m and $R_2$ have the above mentioned meanings, and A is a group of the formulae 2, 3, 5 or 6, B is the thienyl group substituted with $(R)_m$, $R_3$ and $R_4$ are hydrogen, and $R_5$ is a phenyl group or thienyl group substituted with a group $(R)_m$.

The activity of the compounds was determined in some relevant test models, and compared with known anti-ulcer substances, i.e. the histamine $H_2$-antagonists cimetidine and ranitidine:

1a. Inhibition of gastric acid secretion in vitro

In vitro acid secretion was investigated by studying the uptake of the weak base ($^{14}$C)-aminopyrine in intact parietal cells from the stomach of the rabbit. Acid secretion was stimulated by dibutyryl-cyclic-AMP and the inhibition of acid secretion was determined by the decrease of the ($^{14}$C)-aminopyrine accumulation in parietal cells (according to a modification of the method described by T. Berglindh et al., Akta Physiol. Scand. 97, 401, 1976). The results were expressed in $pI_{50}$-values.

1b. Inhibition of gastric acid secretion in vivo

In vivo acid secretion was examined by determining the quantity of acid in the stomach of the pylorus-ligated rat (H. Shay et al., Gastroenterology 5, 43, 1945). Acid secretion was stimulated by subcutaneous administration of histamine. The test substances were administered orally and the inhibition of acid secretion was established by comparison of the quantity of gastric acid produced in 1 hour in treated and untreated animals. The results were expressed in $ID_{50}$-values.

2. Mucosa-protective activity in vivo

In vivo mucosa-protective activity was investigated by studying the protection against ethanol-induced stomach damage in the rat (A. Robert et al., Gastroenterology 77, 433, 1979). The test substances were administered orally and the mucosa-protective activity was established by comparison of the stomach damage caused by ethanol in 1 hour in treated and untreated animals. The results were expressed in $ED_{50}$-values.

.3 Anti-ulcer activity in vivo

The anti-ulcer activity for the most active compounds was determined by studying the protection against differently caused damage of the stomach and the duodenum in the rat. Notably the protection was studied against aspirin, indomethacin and stress induced damage of the stomach and damage of the duodenum induced by cysteamine. The results were expressed in $ED50$-values.

The compounds according to the invention of formula 1 are new compounds with the exception of the compound in which A is a group of formula 2, wherein m is 0, $Q_1$ is oxygen, $R_2$, $R_3$ and $R_4$ are hydrogen and $R_5$ is phenyl. This compound is known from J. Heterocyclic Chem. 20, 1251, (1983).

The compounds may be prepared in a manner known per se for analogous compounds.

Depending on the meanings of the symbols, the compounds of formula 1 can be obtained inter alia by means of one of the following methods.

Compounds of formula 1. wherein A is a group of formula (2) or (5) can be obtained, for example, by converting a compound of formula 11

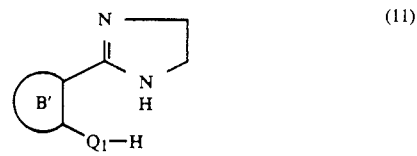

wherein $Q_1$ has the above-mentioned meaning and B' is a phenyl ring substituted with $(R)_m$, or a group B having the above-mentioned meaning, with a compound of formula 12

wherein $R_5$ has the above-mentioned meaning and L is a halogen atom.

The reaction is preferably carried out in an inert solvent, for example, methanol, ethanol, acetonitrile or dimethyl formamide, at a temperature of 0° to 180° C. for 1–48 hours. A base, for example, sodium methoxide, may be added to the reaction mixture.

The compounds of formula 11 are partly known compounds (German Patent Specification 2.034.756 and 2.034.987) and, in so far as they are new compounds, they may be prepared in an analogous manner.

Furthermore, the compounds of formula 1, wherein A is a group of formula (2) or (5), can be obtained by converting a compound of formula 13

wherein A' is the group (2) or (5) and $R_5$ and L have the above-mentioned meanings, with an amine of the general formula (14)

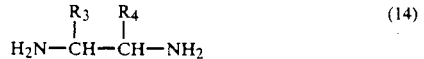

wherein $R_3$ and $R_4$ have the above-mentioned meanings.

The reaction is preferably carried out in an inert solvent for example, acetonitrile or dimethyl sulphoxide, at a temperature of 20° to 200° C. for 1–72 hours.

Some of the compounds of formula 13 are known (Eur.J.Med.Chem.Chim.Ther.20. 425, 1985). In so far as the compounds are new they can be obtained in analogous manners.

Moreover, compounds of formula 13, wherein $Q_1$ (in A') is a sulphur atom can also be obtained in a simple manner known per se from the readily available acid chlorides of formula (Synthesis 670, 1981):

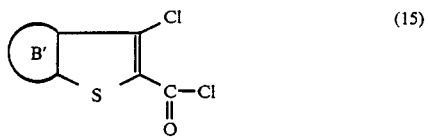

wherein B' has the above-mentioned meaning.

Furthermore, the compounds of formula 1, wherein A is a group of the formulae (2) (10), can be obtained, for example, by converting compounds of formula 16

wherein A and $R_5$ have the above-mentioned meanings, into the corresponding carbamates of formula 17 in a manner known per se (J.Heterocyclic Chem. 20 1251, 1983):

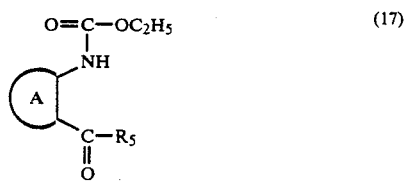

alkylating these with a compound of formula 18

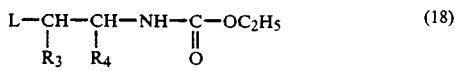

wherein $R_3$, $R_4$ and L have the above-mentioned meanings, then deprotecting the two amino functions, after which the desired compounds of the general formula 1 are obtained by ring closure.

The compounds of formula 1 can also be obtained by alkylation of compounds of formula 16 with N.carbo.tert.butyloxy-aziridine, followed by removal of the tert.butyloxycarbonyl group and ring-closure.

Compounds having formula (19)

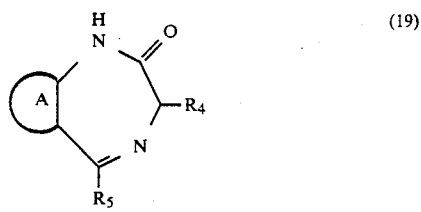

wherein A, $R_4$ and $R_5$ nave the above-mentioned meanings, can be obtained in a manner known per se (J.Heterocyclic Chem 16, 189, 1979) or quite analogous thereto starting with compounds of formula 16. The compound of formula 19 may then be converted into compounds of formula 1 by reduction with, for example, LiAlH$_4$.

The compounds of formula 16 are partly known compounds (J Prakt.Chem. 315. 779, 1973 and J.Org.Chem. 39. 3440, 1974) and, in so far as they are new compounds, they can be obtained in analogous manners.

As last reaction step one or more chemical conversions known per se, for example, reduction reactions, acylation reactions, alkylation reactions, and the like, may be used to obtain the desired compounds of formula 1.

As examples of pharmaceutically acceptable acids with which the compounds of formula 1 can form salts may be mentioned hydrochloric acid, sulphuric acid, phosphoric acid, methanesulphonic acid, p-toluene sulphonic acid, benzoic acid, acetic acid, propionic acid, tartaric acid, succinic acid, citric acid, fumaric acid, maleic acid, etc.

The compounds of formula 1 and the salts thereof can be brought into a form preferably suitable for oral administration, for example, capsules, tablets, coated tablets, and pills, by means of conventionally used techniques and auxiliary substances.

The invention will now be described in greater detail with reference to the ensuing specific examples.

EXAMPLE I 5 (4-chlorophenyl)-2,3-dihydro-1H-benzothieno-3,2-e]-1,4-diazepine hydrobromide A solution of 2-(2-mercaptophenyl)-2-imidazoline (17.8 g; 0.1 mol) and 2-bromo-4'-chloroacetophenone (23.4 g; 0.1 mol) in a mixture of acetonitrile (150 ml) and methanol (50 ml) was heated at 60° C. while stirring for 3 hours.

The reaction mixture was then evaporated under reduced pressure. The residue was dissolved in a mixture of isopropanol (160 ml) and methanol (40 ml) and the reaction mixture was heated at reflux temperature for 5 hours.

The mixture was cooled to room temperature and the precipitate formed was filtered off, washed with isopropanol and liberated from solvent residues. In this manner 32.5 g of 5-(4-chlorophenyl)-2,3-dihydro-1H-benzothieno-[3.2-e]-1,4-diazepine hydrobromide were obtained; melting-point 317°–319° C.

The compounds recorded in the following table A were prepared in an analogous manner:

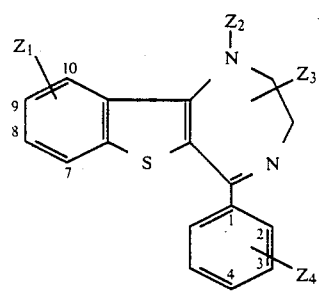

TABLE A

| Comp. no. | $Z_1$ | $Z_2$ | $Z_3$ | $Z_4$ | salt | melting-point (°C.) |
|---|---|---|---|---|---|---|
| 1 | H | H | H | H | HBr | 293–295 |
| 2 | H | H | H | 4-$NO_2$ | HBr | 298–300 |
| 3 | H | H | H | 4-Br | HBr | 285–289 |
| 4 | H | H | H | 4-$OCH_3$ | HBr | 263–265 |
| 5 | H | H | H | 4-OH | HCl | 328–330 |
| 6 | H | H | H | 4-$CF_3$ | HBr | 326–327 |
| 7 | H | H | H | 3-$CF_3$ | free base | 110 ① |
| 8 | H | H | H | 2-$CF_3$ | free base | 90–95 |
| 9 | H | H | H | 4-C≡N | HBr | 312–314 |
| 10 | H | H | H | 4-$COOCH_3$ | HCl | 255–257 |
| 11 | H | H | H | 4-$CH_2OH$ | free base | 220–221 |
| 12 | H | H | H | 2-$OCH_3$ | HBr | 245–248 |
| 13 | H | H | H | 2-OH | HBr | 340–345 |
| 14 | H | H | H | 2-$NO_2$ | HCl | >300 |
| 15 | H | H | H | 2-Cl | free base | 242–246 |
| 16 | 10-F | H | H | 4-Cl | HBr | 290–293 |
| 17 | 9-Cl | H | H | 4-$NO_2$ | HBr | 190–200 |
| 18 | 9-Cl | H | H | 4-F | HBr | >300 |
| 19 | H | H | $CH_3$ | 4-F | HBr | 270–280 |
| 20 | H | H | $CH_3$ | 4-$NO_2$ | HBr | 280–295 |
| 21 | H | $CH_3$ | H | 4-Cl | free base | 157–159 |
| 22 | H | $CH_2COOEt$ | H | 4-Cl | HCl | 214 ① |

23 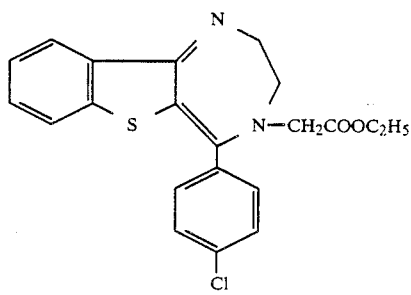  free base  162–164

24 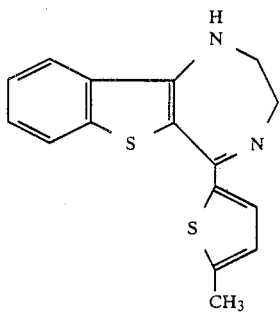  free base  187–188

25 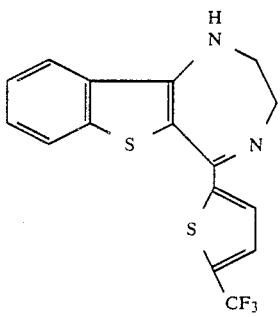  free base  150–160

TABLE A-continued

| Comp. no. | $Z_1$ | $Z_2$ | $Z_3$ | $Z_4$ | salt | melting-point (°C.) |
|---|---|---|---|---|---|---|
| 26 | | | | (structure shown) | free base | 220–225 |
| 27 | | | | (structure shown) | free base | 218–220 |

① = decomposition

EXAMPLE II 5-(4-chlorophenyl)-2,3-dihydro-1H-benzofuro-[3,2-e]-1,4-diazepine

A suspension of 2-(2-hydroxyphenyl)-2-imidazoline (16.2 g; 0.1 mol) and 2-bromo-4'-chloroacetophenone (23.4 g; 0.1 mol) in acetonitrile (180 ml) was heated at 50° C. while stirring for 3 hours. After cooling to room temperature ether (180 ml) was added. The precipitate formed was filtered off and washed with ether (200 ml).

Sodium methoxide (5.4 g; 0.1 mol) was added to a suspension of the resulting product in dimethyl formamide (100 ml) and the mixture was heated at 60° C. while stirring for 4 hours.

A mixture of methanol (35 ml), water (35 ml) and 2N sodium hydroxide (35 ml) was then added. The mixture was cooled to 10° C. and the precipitate formed was filtered off, washed with water and dried.

To a suspension of the product (23.7 g; 0.08 mol) in a mixture of methanol (100 ml) and ether (200 ml) a solution of methanesulphonic acid (7.7 g; 0.08 mol) in ether (50 ml) was added. After addition of petroleum ether (100 ml) the mixture was stirred at 0°–5° C. for 30 minutes. The resulting precipitate was filtered off, washed with ether and dried.

In this manner 27.7 g of 5-(4-chlorophenyl)-2,3-dihydro-1H-benzofuro-[3,2-e]-1,4-diazepine mesylate were obtained; melting-point 226°–227° C.

The compounds mentioned in Tables B and C hereinafter were obtained in an analogous manner.

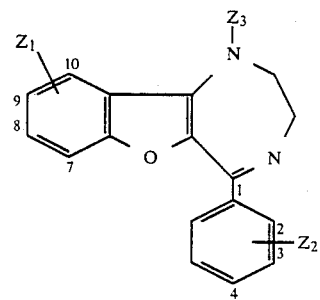

TABLE B

| Comp. no. | $Z_1$ | $Z_2$ | $Z_3$ | salt | melting-point (°C.) |
|---|---|---|---|---|---|
| 28 | H | 4-OCF$_3$ | H | free base | 173–174 |
| 29 | H | 4-Br | H | HCl | 280–281 |
| 30 | H | 2-F | H | free base | 210–211 |
| 31 | H | 4-CF$_3$ | H | HCl | 303–307 |
| 32 | H | 2,4-di-F | H | HCl | 256–258 |
| 33 | H | 3,4-di-Cl | H | HBr | 294–296 |
| 34 | 8-OCH$_3$ | 4-Cl | H | HCl | 200 ① |
| 35 | 9-Br | 4-F | H | free base | 130 ① |
| 36 | 7-F | 4-Cl | H | HCl | 205 |
| 37 | 8-F | 4-Cl | H | free base | 145–147 |
| 38 | 7-Cl | 4-F | H | free base | 179–181 |
| 39 | 8-Cl | 4-F | H | free base | 130 ① |
| 40 | 9-OCH$_3$ | 4-Cl | H | free base | 181–183 |
| 41 | 9-OH | 4-Cl | H | HBr | 203–205 |
| 42 | H | 4-Cl | CH$_3$ | free base | 109–111 |
| 43 | H | 4-Cl | benzyl | HCl | 230–231 |

TABLE B-continued

| Comp. no. | Z₁ | Z₂ | Z₃ | salt | melting-point (°C.) |
|---|---|---|---|---|---|
| 44 | | | 3-amino-benzofuran-2-yl with thiophene-2-yl imine, diazepine | HCl | 260 |
| 45 | | | 3-amino-benzofuran-2-yl with 5-methylthiophene-2-yl imine, diazepine | free base | 100–105 |
| 46 | | | 3-amino-benzofuran-2-yl with thiophene-3-yl imine, diazepine | free base | 110–120 |
| 47 | | | 3-amino-benzofuran-2-yl with CH₂—CH₂-(4-fluorophenyl) imine, diazepine | HBr | 210 |
| 48 | | | 3-amino-benzofuran-2-yl with CH=CH-(4-fluorophenyl) imine, diazepine | free base | 170–180 |
| 49 | | | 3-amino-benzofuran-2-yl with (CH₂)₅—CH₃ imine, diazepine | HCl | 218–219 |

① = decomposition

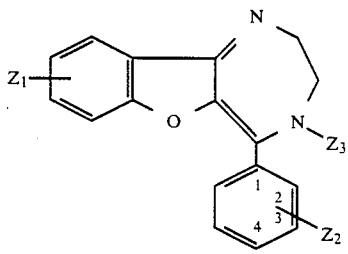

TABLE C

| Comp. no. | $Z_1$ | $Z_2$ | $Z_3$ | salt | melting-point (°C.) |
|---|---|---|---|---|---|
| 50 | H | 4-Cl | $CH_3$ | free base | 176–178 |
| 51 | H | 4-Cl | $COCH_3$ | free base | 179–181 |
| 52 | H | 4-Cl | $COOC_2H_5$ | free base | 132–133 |
| 53 | H | 4-Cl | $C_2H_5$ | HCl | 255–256 |
| 54 | H | 4-Cl | benzyl | HCl | 150 ⓓ |

ⓓ = decomposition

EXAMPLE III

8-fluoro-5-(4-chlorophenyl)-2,3-dihydro-1H-benzo-thieno-[3.2-e]-1,4-diazepine Ethylene diamine (12 g; 0.2 mol) was added to a solution of 6-fluoro-3-chloro-2-(4-chlorobenzoyl)-benzo[b]thiophene (32.5 g; 0.1 mol) (obtained by conversion of 6-fluoro-3-chlorobenzo[b]thiophene carboxychloride into the corresponding methoxymethyl amide and then into the desired ketone by means of 4-chlorophenyl-magnesium bromide (see Tet. Letters 22, 3815, 1981)) and the reaction mixture was heated at 60° C. while stirring for 24 hours. After cooling to room temperature, ether (100 ml) and 2N hydrochloric acid (250 ml) were added and the reaction mixture was stirred at room temperature for 3 hours.

The ether layer was separated and the acidic water layer was washed once more with ether. (From the collected ether layers 22.7 g (0.07 mol) of the starting substance were obtained by evaporation). The resulting water layer was made alkaline with 2N sodium hydroxide (250 ml) and the precipitate formed was filtered off.

After recrystallization from acetonitrile 5.9 g of 8-fluoro-5-(4-chlorophenyl)-2,3-dihydro-1H-benzo-thieno-[3,2-e]-1,4-diazepine were obtained; melting-point 198°–199° C.

The compounds mentioned in Table D hereinafter were obtained in an analogous manner.

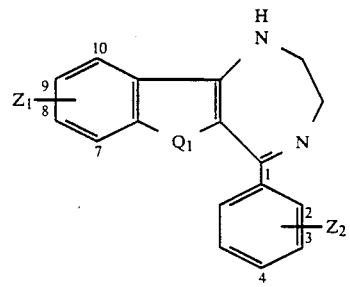

TABLE D

| Comp. no. | $Q_1$ | $Z_1$ | $Z_2$ | salt | melting-point (°C.) |
|---|---|---|---|---|---|
| 55 | S | 10-Cl | 4-Cl | free base | 172–173 |
| 56 | S | H | 4-F | free base | 250–251 |
| 57 | S | H | 3-Cl | free base | 198–200 |
| 58 | S | 9-F | 4-Cl | free base | 192–193 |
| 59 | S | 8-$OCH_3$ | 4-Cl | free base | 164–166 |
| 60 | S | 8-$CF_3$ | 4-Cl | free base | 215 |
| 61 | S | 8-$CH_3$ | 4-Cl | free base | 225 |
| 62 | S | 8-C≡N | 4-Cl | HCl | 282–284 |
| 63 | S | 7-F | 4-Cl | free base | 95 ⓓ |
| 64 | S | 8-F | 4-$CF_3$ | free base | 109 |
| 65 | S | 9-F | 4-$CF_3$ | HCl | 296–300 |
| 66 | S | 9-F | 4-F | HCl | >300 |
| 67 | S | 10-$CH_3$ | 4-Cl | free base | 161–163 |
| 68 | S | 9-Cl | 4-Cl | HCl | >300 |
| 69 | S | 7-Cl | 4-Cl | HCl | >300 |
| 70 | S | 9-$CF_3$ | 4-Cl | free base | 132–142 |
| 71 | S | H | 4-$N(CH_3)_2$ | free base | 150 ⓓ |
| 72 | S | 8,9-$OCH_2O$ | 4-Cl | free base | 190 ⓓ |
| 73 | S | 9-F | 4-$OCH_3$ | HCl | 289–291 |
| 74 | O | 9-$NO_2$ | 4-Cl | HCl | >300 |
| 75 | O | 9-$NH_2$ | 4-Cl | HCl | >300 |
| 76 | O | 9-C≡N | 4-Cl | HCl | >300 |
| 77 |  |  |  | HCl | 150 ⓓ |

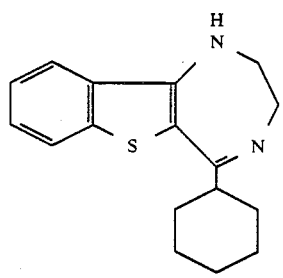

TABLE D-continued

| Comp. no. | Q₁ | Z₁ | Z₂ | salt | melting-point (°C.) |
|---|---|---|---|---|---|
| 78 | | | (structure) | HCl | >300 |
| 79 | | | (structure) | free base | 130–140 |
| 80 | | | (structure) | HCl | 260 |
| 81 | | | (structure) | free base | 259–261 |
| 82 | | | (structure) | HCl | >300 |

① = decomposition

EXAMPLE IV 5-(4-fluorophenyl)-2,3-dihydro-1H-benzofuro-[3,2-e]-1,4-diazepine

Ethyl chloroformate (32.5 g; 0.3 mol) was added dropwise to a solution of 3-amino-2-(4-fluorobenzoyl)-benzo[b]furan (25.5 g; 0.1 mol) in benzene (300 ml) and pyridine (60 ml). After stirring overnight at room temperature the reaction mixture was extracted with 1N hydrochloric acid (200 ml), 1N sodium hydroxide (200 ml), water (100 ml) and brine (50 ml). The organic layer was dried on sodium sulphate and evaporated under reduced pressure.

The resulting product (approx. 29 g) was added to a suspension of 55% sodium hydride (6.5 g; 0.15 mol) in dimethyl formamide (250 ml). After the occurring gas evolution had stopped, 22.7 g (0.15 mol) of ethyl N-(2-chloroethyl)carbamate were added dropwise. After stirring at 60° C. for 16 hours, the reaction mixture was poured on ice and extracted three times with ethyl acetate (3×250 ml). The collected organic layers were extracted with water (100 ml) and with brine (50 ml), dried on sodium sulphate and evaporated under reduced pressure.

A solution of the resulting product (approx. 27 g) in a 45% HBr-acetic acid mixture (150 ml) was heated at 65° C. for 4 hours. After cooling the reaction mixture was poured on ice, made alkaline with aqueous ammonia and extracted twice with dichloromethane (2×500 ml). The collected organic layers were washed with water (100 ml), dried on sodium sulphate and evaporated under reduced pressure.

A solution of the resulting product (approx. 21 g) and a 50% sodium hydroxide solution (50 ml) in absolute ethanol (500 ml) was heated at reflux temperature for 90 minutes. After cooling the reaction mixture was poured on ice and extracted three times with dichloromethane (3×300 ml). The collected organic layers were washed with water (100 ml), dried on sodium sulphate and evaporated under reduced pressure. The resulting crude product was purified by means of flash chromatography over 1500 g of silica gel using a mixture of dichloromethane, methanol and ammonia in the ratio 87:12.5:0.5 as an eluent. After evaporating the collected fractions under reduced pressure, 10.0 g of 5-(4-fluorophenyl)-2,3-dihydro-1H-benzofuro-[3,2-e]-1,4-diazepine were obtained; melting-point 144°-148° C. The compound no. 83 of the formula

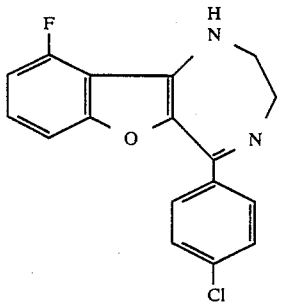

was obtained in an analogous manner as a free base having a melting-point of 147°-149° C.

EXAMPLE V

5(4-trifluoromethyl)-6-phenyl-2,3-dihydro-1H-thieno-[2,3e]-1,4-diazepine

A mixture of 2 amino-3-(4-trifluoromethylbenzoyl)-4-phenylthiophene (6.9 g; 20 mmol) and N-carbo-tert-.butyloxyaziridine (11 ml) and p-toluenesulphonic acid (70 mg) was heated at 130° C. for 14 hours. After cooling ether (150 ml) was added to the reaction mixture. The solution was washed with sodium bicarbonate solution (50 ml, 5%) and with brine (50 ml). The organic layer was dried on sodium sulphate and evaporated under reduced pressure. The resulting crude product was purified chromatographically by means of flash chromatography over 200 g of silicagel using a mixture of ether and petroleum ether in the ratio 1:1 as an eluent. After evaporating the collected fractions under reduced pressure, 2.6 g of pure product were obtained.

A solution of the obtained product (2.6 g; 5.4 mmol) in 3N hydrochloric acid (60 ml) was heated at 100° C. for 90 minutes. The reaction mixture was poured on ice, made alkaline with ammonia and extracted three times with ethyl acetate (3×100 ml). The organic layer was dried on sodium sulphate and evaporated under reduced pressure. The resulting crude product was purified chromatographically by means of flash chromatography over 100 g of silicagel using dichloromethane/methanol/ammonia (93/6.5/0.5) as an eluent. After evaporating the collected fractions under reduced pressure, 0.54 g of pure product were obtained.

A solution of the obtained pure product (0.54 g; 1.4 mmol) in pyridine (10 ml), benzene (15 ml) and acetic acid (0.085 g; 1.4 mmol) was heated at reflux temperature for 24 hours while water was separated by means of a Dean-Stark-trap. After cooling the reaction mixture was evaporated under reduced pressure. The resulting crude product was purified by means of flash chromatography over 80 g of silicagel using dichloromethane/methanol/ammonia (95/4.5/0.5) as an eluent. After evaporating the collected fractions under reduced pressure 0.23 g of crystalline 5-(4-trifluoromethyl)-6-phenyl-2,3-dihydro-1H-thieno[2,3-e]-1,4-diazepine were obtained; melting point 124°-124.5° C.

EXAMPLE VI 5-(4-chlorophenyl)-2,3-dihydro-1H-benzothieno-[2.3-e]-1,4-diazepine A solution of 2-amino-3-(4-chlorophenyl)benzo[b]thiophene (28.8 g; 0.1 mol) (Chem.Ber. 101. 1933, 1968) and chloroacetyl chloride (24 8 g; 0.22 mol) in chloroform (350 ml) was heated at reflux temperature for 1 hour and then evaporated under reduced pressure.

A solution of the resulting product (approx. 35 g) and NaI (16.5 g; 0.11 mol) in acetone (500 ml) was heated at reflux temperature for 90 minutes. After cooling to room temperature the NaCl formed was filtered off and the filtrate was evaporated under reduced pressure.

Ammonia gas was led through a solution of the resulting product (approx. 44 g) in a mixture of chloroform (450 ml) and methanol (50 ml) for 3 hours. After stirring at room temperature for another 90 minutes the reaction mixture was extracted with ice-water (250 ml), with a sodium bicarbonate solution (100 ml, 5%). and with brine (100 ml). The organic layer was dried on sodium sulphate and evaporated under reduced pressure.

A solution of the resulting product (approx. 33 g) and acetic acid (6 g; 0.1 mol) in a mixture of pyridine (180 ml) and benzene (200 ml) was heated at reflux temperature for 2.5 hours while water was separated by means of a Dean-Stark-trap. The reaction mixture was evaporated under reduced pressure. The residue was dissolved in dichloromethane (500 ml) and the solution was extracted with a sodium bicarbonate solution (200 ml, 2.5%), with water (200 ml) and with brine (100 ml). The organic layer was dried on sodium sulphate and evaporated under reduced pressure. The resulting crude product was purified chromatographically by means of flash chromatography over 1500 g of silicagel using a mixture of dichloromethane and acetone in the ratio 9:1 as an eluent. After evaporating the collected fractions under reduced pressure, 13.3 g of pure product were obtained.

A solution of the resulting product (13.3 g; 0.04 mol) in tetrahydrofuran (200 ml) was added to a suspension of 7.6 g of lithium aluminium hydride (0.2 mol) in tetrahydrofuran (500 ml). The reaction mixture was stirred at room temperature for 1 hour and then at 50° C. for 30 minutes. After cooling, 7.6 ml of water in 50 ml of tetrahydrofuran, 15.2 ml of 2N sodium hydroxide and 15.2 ml of water, successively, were added dropwise. After stirring at room temperature for a few hours the precipitate formed was filtered off and washed with tetrahydrofuran. The filtrate was evaporated under reduced pressure. The resulting crude product was purified by means of flash chromatography over 1000 g of silicagel using a mixture of dichloromethane, methanol and ammonia in the ratio 90.5:9:0.5 as an eluent. After evaporating the collected fractions under reduced pressure, 8.0 g of crystalline 5-(4-chlorophenyl)-2,3-dihydro-1H-benzothieno-[2,3-e]-1,4-diazepine were obtained the crystal lattice of which comprised 1 mol equivalent of tetrahydrofuran; melting-point 260° C.

The compounds mentioned in table E were prepared in a similar manner:

TABLE E

| Comp. no. | Structure | Salt | Melting point (°C.) |
|---|---|---|---|
| 84 | | free base | 132 |
| 85 | | free base | 160① |
| 86 | | HBr | 200 |
| 87 | 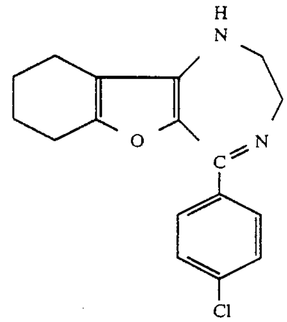 | free base | 169–170 |
| 88 | 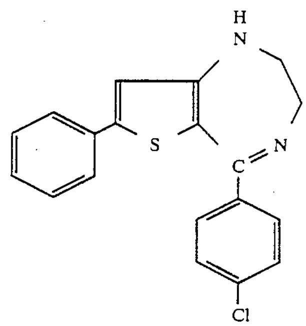 | HBr | >300 |
| 89 | 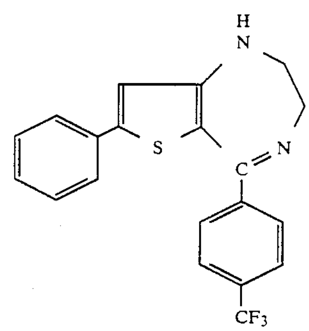 | HBr | 264 |
| 90 | 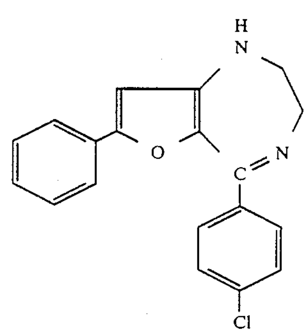 | free base | 170① |

TABLE E-continued

| Comp. no. | Structure | Salt | Melting point (°C.) |
|---|---|---|---|
| 91 | 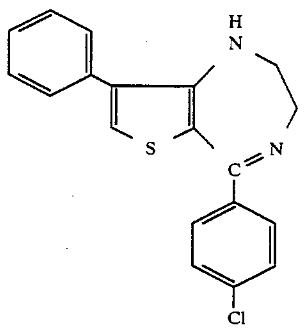 | free base | 120① |
| 92 | 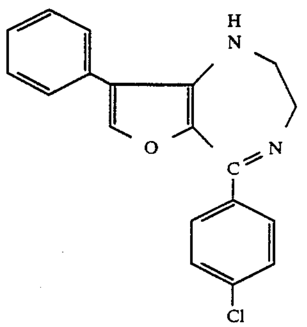 | HBr | >300 |

① = decomposition

I claim:
1. Compounds of formula (1)

|  | C % | H % | N % |
|---|---|---|---|
| Calculated | 42.25 | 2.66 | 8.21 |
| Found | 42.37 | 2.58 | 8.39 |

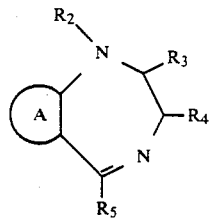

wherein the symbols have the following meanings:
A together with the two carbon toms of the seven membered ring, forms a group selected from the formulae (2), (3), (4) and (7)

|  | C % | H % | N % |
|---|---|---|---|
| Calculated | 43.53 | 2.44 | 8.46 |
| Found | 43.47 | 2.28 | 8.64 | wherein
R is halogen, alkyl, alkoxy, alkylthio, amino, mono- or dialkylamino, hydroxyalkyl, alkylcarbonyl, aminocarbonyl, mono- or dialkylamino carbonyl, alkoxycarbonyl, nitro, cyano, trifluoromethyl, trifluoromethoxy, alkylsulphonyl, aminosulphonyl, hydroxy, phenyl or benzoyl, and m has the value 0-4, or $(R)_m$ is alkylene dioxy, $Q_1$ is oxygen or sulphur, n has the value 3 or 4;

$R_2$ is hydrogen, alkyl, phenylalkyl, alkylcarbonyl, aminocarbonyl, mono- or dialkylaminocarbonyl, alkoxycarbonyl or alkoxycarbonylalkyl;

$R_3$ and $R_4$ independently of each other are hydrogen, alkyl or hydroxy; and $R_5$ is phenyl, thienyl, cyclopentyl, cyclohexyl, n-pentyl, n-hexyl, benzyl, phenethyl, phenylethynyl, phenylamino, or benzylamino, which groups may be substituted with the group $(R)_m$, with the proviso that R cannot be halogen or hydroxy if the substituent is bonded to a nitrogen atom, and with the proviso that if m has the value 0, $Q_1$ is oxygen, $R_2$, $R_3$ and $R_4$ are hydrogen and $R_5$ is phenyl, A cannot be a group of formula (2).

2. Compounds as claimed in claim 1, characterized in that R, $Q_1$, m and $R_2$ have the meanings mentioned in claim 17, A is a group of formula (2) or (3), B is the thienyl group substituted with $(R)_m$, $R_3$ and $R_4$ are hydrogen atoms, and $R_5$ is a phenyl group or thienyl group substituted with $(R)_m$.

3. Pharmaceutical compositions having anti-ulcer activity which comprise an effective amount of at least one compound of formula (1) as an active substance

|  | C % | H % | N % |
|---|---|---|---|
| Calculated | 57.93 | 4.86 | 9.65 |
| Found | 57.95 | 5.05 | 9.55 |

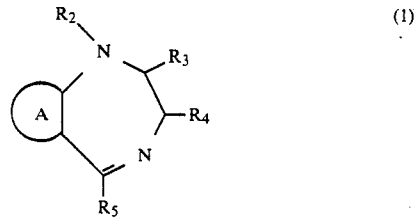

wherein the symbols have the following meanings:
A together with the two carbon atoms of the seven membered ring, forms a group selected from the groups of the formulae (2), (3), (4) and (7)

|  | C % | H % | N % |
|---|---|---|---|
| Calculated | 53.57 | 4.80 | 8.33 |
| Found | 53.28 | 4.91 | 8.21 |

|  | C % | H % | N % |
|---|---|---|---|
| Calculated | 43.53 | 2.44 | 8.46 |
| Found | 43.47 | 2.28 | 8.64 | wherein
R is halogen, alkyl, alkoxy, alkylthio, amino, mono- or dialkylamino, hydroxyalkyl, alkylcarbonyl, aminocarbonyl, mono- or dialkylamino carbonyl, alkoxycarbonyl, nitro, cyano, trifluoromethyl, trifluoromethyl, alkylsulphonyl, aminosulphonyl, hydroxy, phenyl or benzoyl, and m has the value 0-4, or $(R)_m$ is alkylene dioxy, $Q_1$ is oxygen or sulphur, n has the value 3 or 4;

$R_2$ is hydrogen, alkyl, phenylakyl, alkylcarbonyl, aminocarbonyl, mono- or dialkylaminocarbonyl, alkoxycarbonyl or alkoxycarbonylalkyl;

$R_3$ and $R_4$ independently of each other are hydrogen, alkyl or hydroxy; and $R_5$ is phenyl, thienyl, cyclopentyl, cyclohexyl, n-pentyl, n-hexyl, benzyl, phenethyl, phenylethynyl, phenylamino, or benzylamino, which groups may be substituted with the group $(R)_m$ with the proviso that R cannot be halogen or hydroxy if the substituent is bonded to a nitrogen atom, or a salt thereof with a pharmacologically acceptable acid and auxiliary substances.

4. Compositions as claimed in claim 3, characterized in that a compound of formula (1) is used as an active substance, wherein R, $Q_1$, m and $R_2$ have the meanings mentioned in claim 12, A is a group of formula (2) or (3), $R_3$ and $R_4$ are hydrogen, and $R_5$ is the phenyl group or thienyl group substituted with $(R)_m$, and salts thereof with pharmacologically acceptable acids.

* * * * *

UNITED STATES PATENT AND TRADEMARK OFFICE
CERTIFICATE OF CORRECTION

PATENT NO. : 4,985,423
DATED : January 15, 1992
INVENTOR(S) : Jacobus A. J. DEN HARTOG et al It is certified that error appears in the above-identified patent and that said Letters Patent is hereby corrected as shown below:

Claim 1, column 21, lines 36-40, cancel the table;

lines 56-61, cancel the table and in its place insert the formulae as shown on the attached page.

Claim 2, column 22, line 21, change "17," to read --1,--;

lines 21-22, cancel "B is the thienyl group substituted with $(R)_m$,".

Claim 3, column 22, lines 28-32, cancel the table;

lines 50-59, cancel both tables, and in their place insert the formula as shown on the attached page.

Claim 4, column 24, line 7, change "12," to read --3,--.

Signed and Sealed this

Twenty-third Day of November, 1993

Attest:

*Attesting Officer*

BRUCE LEHMAN

*Commissioner of Patents and Trademarks*

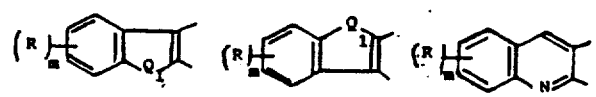
(2)   (3)   (4)
(7)